US009357291B2

(12) United States Patent
Lang et al.

(10) Patent No.: US 9,357,291 B2
(45) Date of Patent: May 31, 2016

(54) MASS PORTS FOR TUNING FREQUENCY RESPONSES

(71) Applicant: Skullcandy, Inc., Park City, UT (US)

(72) Inventors: James Lang, San Francisco, CA (US); Samuel Steele Noertker, Park City, UT (US); Harry Van, San Francisco, CA (US)

(73) Assignee: SkullCandy, Inc., Park City, UT (US)

( * ) Notice: Subject to any disclaimer, the term of this patent is extended or adjusted under 35 U.S.C. 154(b) by 0 days.

(21) Appl. No.: 14/465,269

(22) Filed: Aug. 21, 2014

(65) Prior Publication Data

US 2016/0057531 A1 Feb. 25, 2016

(51) Int. Cl.
*A61B 7/02* (2006.01)
*H04R 1/32* (2006.01)

(52) U.S. Cl.
CPC .................................... *H04R 1/323* (2013.01)

(58) Field of Classification Search
CPC .................................................... A61F 11/008
USPC .......................... 181/132, 135, 121, 198, 199
See application file for complete search history.

(56) References Cited

U.S. PATENT DOCUMENTS 5,109,422 A * 4/1992 Furukawa ....................... 381/96
6,704,429 B2 * 3/2004 Lin ............................... 381/380
6,810,987 B1 * 11/2004 DeKalb ......................... 181/129
7,840,022 B2 * 11/2010 Matsumura et al. .......... 381/345
7,928,303 B2 * 4/2011 Millender et al. .......... 84/411 R
2006/0002569 A1 * 1/2006 Dickie ............................ 381/89
2014/0003645 A1 * 1/2014 Silver et al. ................... 381/351
2014/0133668 A1 * 5/2014 Podoloff ......................... 381/74
2015/0172800 A1 * 6/2015 Azmi et al. .................... 381/380

FOREIGN PATENT DOCUMENTS

JP S54-170126 U 12/1979
JP S57-034796 U 2/1982
JP H02-294198 A 12/1990

OTHER PUBLICATIONS

Extended European Search Report dated Nov. 23, 2015 as received in Application No. 15182053.7, 10 pgs.

* cited by examiner

*Primary Examiner* — Forrest M Phillips
(74) *Attorney, Agent, or Firm* — Maschoff Brennan

(57) ABSTRACT

A mass port configured to tune a frequency response of an audio reproduction device is disclosed. The mass port includes a head portion and an insertion portion coupled to the head portion. The head portion includes a sealing structure on a rear side. The head portion is configured to attach to a rear plate of a driver at the sealing structure. The insertion portion is configured to be inserted into a speaker port on the rear plate of the driver. The head portion and the insertion portion include an air slot that runs through the head portion and the insertion portion.

20 Claims, 13 Drawing Sheets

500

S1343.10005US01
Sheet 13 of 13

MASS PORTS FOR TUNING FREQUENCY RESPONSES

BACKGROUND

The specification relates to audio reproduction devices. In particular, the specification relates to attaching a mass port to an audio reproduction device for tuning a frequency response of the audio reproduction device.

A user may listen to music using a pair of headphones. The user may like to improve sound quality in the pair of headphones. For example, a first user may like to increase bass in the sound while a second user may like to reduce bass in the sound. It may be desirable to provide headphones to users that satisfy each individual user's personal preference.

SUMMARY

According to one innovative aspect of the subject matter described in this disclosure, a mass port for tuning a frequency response of an audio reproduction device includes a head portion and an insertion portion coupled to the head portion. The head portion includes a sealing structure on a rear side. The head portion may be configured to attach to a rear plate of a driver at the sealing structure. The insertion portion may be configured to be inserted into a speaker port on the rear plate of the driver. The head portion and the insertion portion include an air slot that runs through the head portion and the insertion portion.

According to another innovative aspect of the subject matter described in this disclosure, a mass port for tuning a frequency response of an audio reproduction device includes an insertion portion and a head portion. The insertion portion may have a shape of a cylinder. The insertion portion may be configured to be inserted into a speaker port on a rear plate of a driver. The insertion portion may include a diameter of 3.7 millimeters and a length of 4.94 millimeters. The head portion may have a shape of a disc. The head portion may include a diameter of 10 millimeters and a thickness of 0.8 millimeters. The head portion may include a sealing structure and may be configured to attach to the rear plate of the driver at the sealing structure. The head portion and the insertion portion include an air slot that runs through a center of the head portion and a center of the insertion portion along a longitudinal axis. The air slot may include a diameter of 1.5 millimeters.

According to yet another innovative aspect of the subject matter described in this disclosure, a mass port for tuning a frequency response of an audio reproduction device includes a slotted disc. The slotted disc includes an air slot and glue areas on a rear side of the slotted disc. The air slot may include a closed end and an open end. The closed end of the air slot may be configured to block air flow between the air slot and a surrounding environment. The open end of the air slot may be configured to permit air flow between the air slot and the surrounding environment. The slotted disc may be configured to glue to a rear plate of a driver at the glue areas to form an air flow path from a speaker port of the rear plate toward the closed end of the air slot and toward the open end of the air slot. The closed end of the air slot may be configured to align with the speaker port of the rear plate.

Other aspects include corresponding methods, systems, apparatus, and computer program products for these and other innovative aspects.

These and other implementations may each optionally include one or more of the following features. For instance, the features include: the head portion including a disc and the air slot penetrating a center of the disc; the disc including a diameter of 10 millimeters and a thickness of 0.8 millimeters; the insertion portion including a cylinder and the air slot penetrating a center of the cylinder along a longitudinal axis of the cylinder; the cylinder including a diameter of 3.7 millimeters and a length of 4.94 millimeters; the head portion and the insertion portion being formed by a single piece of material; the single piece of material including a piece of plastic; the air slot including a diameter of 1.5 millimeters; the air slot including a diameter in a range between 0.75 millimeters and 2 millimeters; the sealing structure including a glue moat; the glue moat including a width of 0.5 millimeters and a depth of 0.3 millimeters; a distance between an outer edge of the head portion and the glue moat including 2.25 millimeters; a size of the air slot being configured to be modifiable to tune a frequency response of the driver; the air slot including a funnel with two conical ends; the slotted disc including a diameter of 23 millimeters; the air slot including a width of 5 millimeters and a height of 2.5 millimeters; a center of the slotted disc being configured to align with a center of the rear plate of the driver; and a size of the air slot being configured to be modifiable to tune a frequency response of the driver.

The present disclosure is particularly advantageous in numerous respects. For example, by mounting a mass port on a rear plate of a driver in an audio reproduction device, a frequency response of the audio reproduction device may be altered, which allows use of a single driver with multiple frequency responses. Different mass ports with different air slot sizes may be configured for the audio reproduction device so that the frequency response of the audio reproduction device may be tuned by mounting the different mass ports to the audio reproduction device, respectively. The inclusion of the mass port in the audio reproduction device may increase acoustic mass and dampening of the driver. A resonance response of the driver may be decreased. Thus, a sound quality of the audio reproduction device may be improved. For example, a bass quality of the audio reproduction device may be improved. The inclusion of the mass port in the audio reproduction device may provide an economic, fast, and simple way for tuning the frequency response of the audio reproduction device. The advantages of the system described herein are provided by way of example, and the system may have numerous other advantages.

BRIEF DESCRIPTION OF THE DRAWINGS

The specification is illustrated by way of example, and not by way of limitation in the figures of the accompanying drawings in which like reference numerals are used to refer to similar elements.

DETAILED DESCRIPTION

Figure 1A:
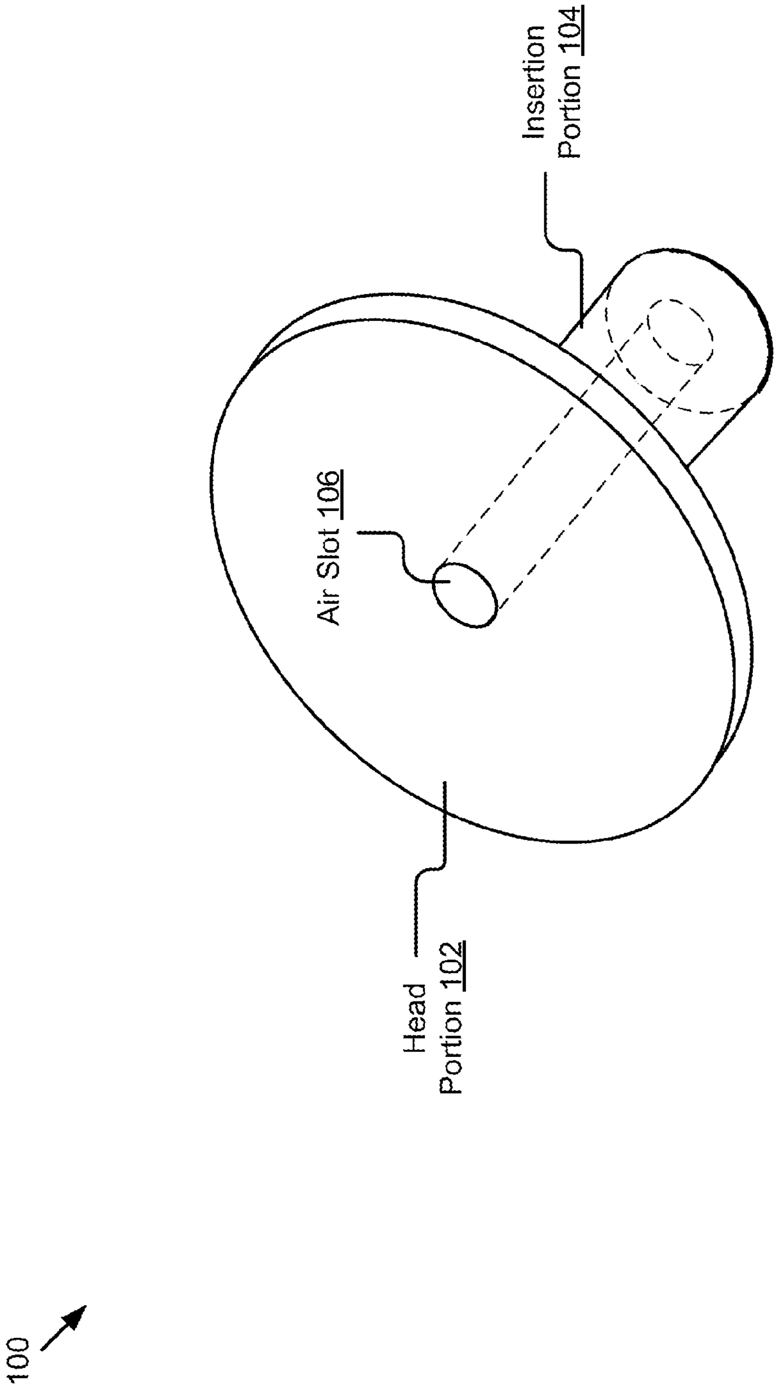
FIGS. 1A and 1B illustrate different views of an example mass port according to some implementations.

Implementations described herein generally relate to mass ports for tuning frequency responses of audio reproduction devices.

In some implementations, a mass port may have a shape similar to a thumbtack and may be referred to as a thumbtack mass port. The thumbtack mass port may include a head portion in a shape of a disc and an insertion portion in a shape of a cylinder. The thumbtack mass port may be mounted on a rear plate of a driver of an audio reproduction device by: (1) inserting the insertion portion into a speaker port in the rear plate; and (2) gluing the head portion to the rear plate. The thumbtack mass port may include an air slot that may penetrate the thumbtack mass port and may run through a center of the head portion and a center of the insertion portion along a longitudinal axis. Air may travel through the air slot in the mass port. In some implementations, the air slot may have a diameter of 1.5 millimeters. Alternatively, the air slot may have another suitable diameter value greater than or less than 1.5 millimeters. The size (e.g., the diameter) of the air slot may be modified to tune a frequency response of the audio reproduction device that the thumbtack mass port is configured to mount on. For example, the size of the air slot may be increased to reduce a resonant response of the audio reproduction device and to improve bass quality of the audio reproduction device.

Alternatively, a mass port may have a shape similar to a disc with an air slot on a rear side of the disc and may be referred to as a slotted disc. The air slot may include a closed end and an open end. The slotted disc may be configured to mount on a rear plate of a driver of an audio reproduction device by gluing the rear side of the slotted disc to the rear plate of the driver. The closed end of the air slot may align with a speaker port in the rear plate so that an air flow path may be formed from the speaker port of the rear plate toward the closed end of the air slot and then toward the open end of the air slot and vice versa. A size of the air slot (e.g., a width or a height of the air slot) may be modified to tune a frequency response of the audio reproduction device that the slotted disc is configured to mount on.

An audio reproduction device described herein may refer to any type of audio reproduction device such as a headphone device, an ear bud device, a speaker dock, a speaker system, a super-aural and a supra-aural headphone device, an in-ear headphone device, a headset or any other audio reproduction device. In some implementations, the audio reproduction device may include a cup, an ear pad coupled to a top edge of the cup, and a driver coupled to the inner wall of the cup.

Reference will now be made to the drawings to describe various aspects of some example implementations of the disclosure. The drawings are diagrammatic and schematic representations of such example implementations, and are not limiting of the disclosure, nor are they necessarily drawn to scale.

Figure 1B:
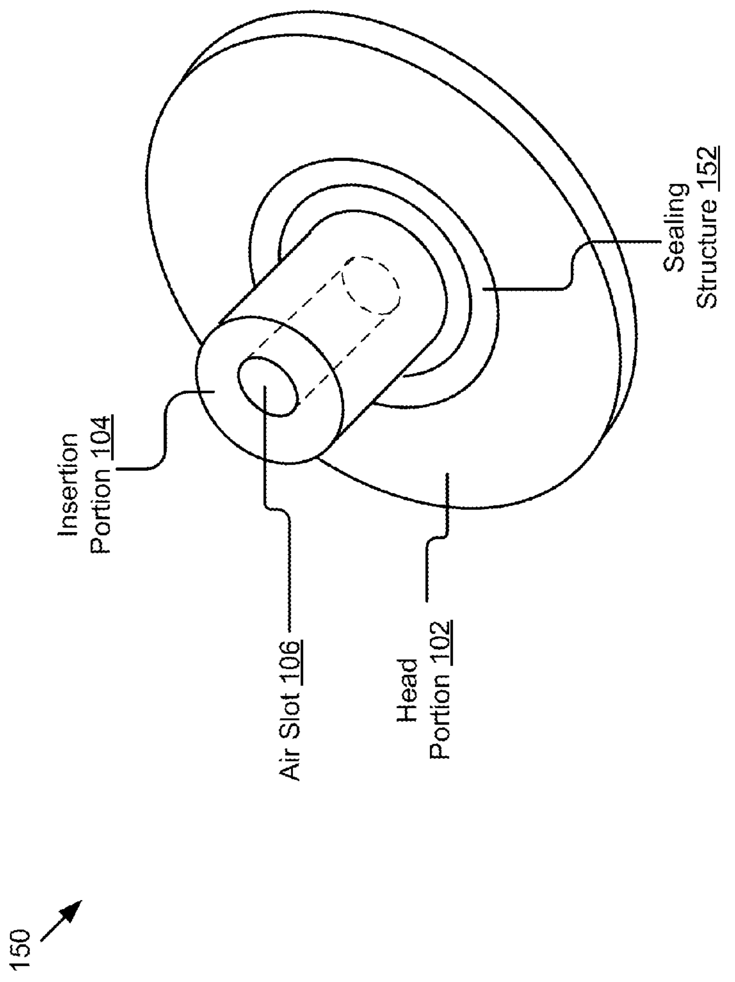

FIGS. 1A and 1B illustrate two different views 100 and 150 of an example mass port according to some implementations. Referring to FIG. 1A, the mass port includes a head portion 102 and an insertion portion 104. FIG. 1A includes a front view of the head portion 102 and a side view of the insertion portion 104. In some implementations, the head portion 102 may be in a shape of a disc. Alternatively, the head portion 102 may be in any other shape such as a cube, a cuboid, a dome, or another suitable shape. In some implementations, the insertion portion 104 may be in a shape of a cylinder. Alternatively, the insertion portion 104 may be in a shape of a cuboid, a cone, a cube, or another suitable shape.

The mass port may include an air slot 106. The air slot 106 may include a funnel that penetrates the mass port and runs through a center of the head portion 102 and a center of the insertion portion 104 along a longitudinal axis. The air slot 106 may have a circular shape with a diameter between 0.75 millimeters (mm) and 2 millimeters. For example, the air slot may have a diameter of about 1.5 millimeters. As used herein, the term "about" as applied to a value may indicate a range of ±10% of the stated value. Alternatively, the air slot 106 may have a diameter with another suitable value. Other dimensions for the air slot 106 are possible. In some implementations, the two ends of the air slot 106 may have a conical shape, and diameters at the two ends of the air slot 106 may be larger than diameters in the middle of the air slot 106.

In some implementations, the mass port formed by the head portion 102 and the insertion portion 104 may have a shape similar to a thumbtack. In some implementations, the head portion 102 and the insertion portion 104 of the mass port may be formed by a single piece of material such as a single piece of plastic (e.g., acrylonitrile butadiene styrene (ABS)). Alternatively, the head portion 102 may be attached to the insertion portion 104 using glue or other mechanical coupling approaches.

The mass port may be coupled to a speaker port of a rear plate of a driver. For example, the insertion portion 104 of the mass port may be inserted into a speaker port of a rear plate of a driver as illustrated in FIGS. 2B and 2C. Dimensions of the mass port are illustrated with reference to FIG. 3.

Referring to FIG. 1B, a rear view of the head portion 102 is illustrated. The rear side of the head portion 102 includes a sealing structure 152 for attaching the head portion 102 to a rear plate of a driver. For example, the sealing structure 152 may include a glue moat that may be filled with glue for attaching the mass port to the rear plate of the driver. Dimensions of the sealing structure 152 are illustrated with reference to FIG. 3. A rear view and a side view of the insertion portion 104 are also illustrated in FIG. 1B, with the air slot 106 running through the insertion portion 104 and the head portion 102.

Figure 2A:
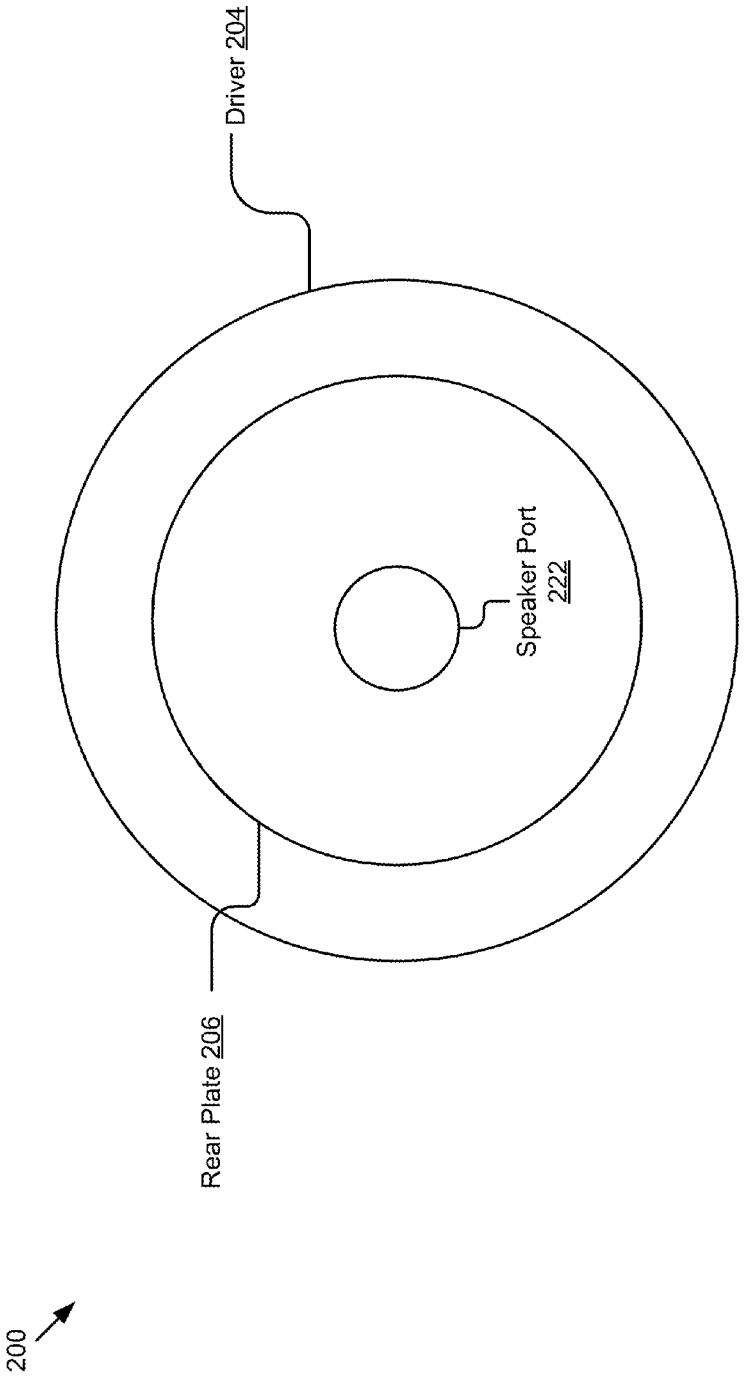
FIG. 2A illustrates an example speaker port in a rear plate of a driver according to some implementations.
Figure 2B:
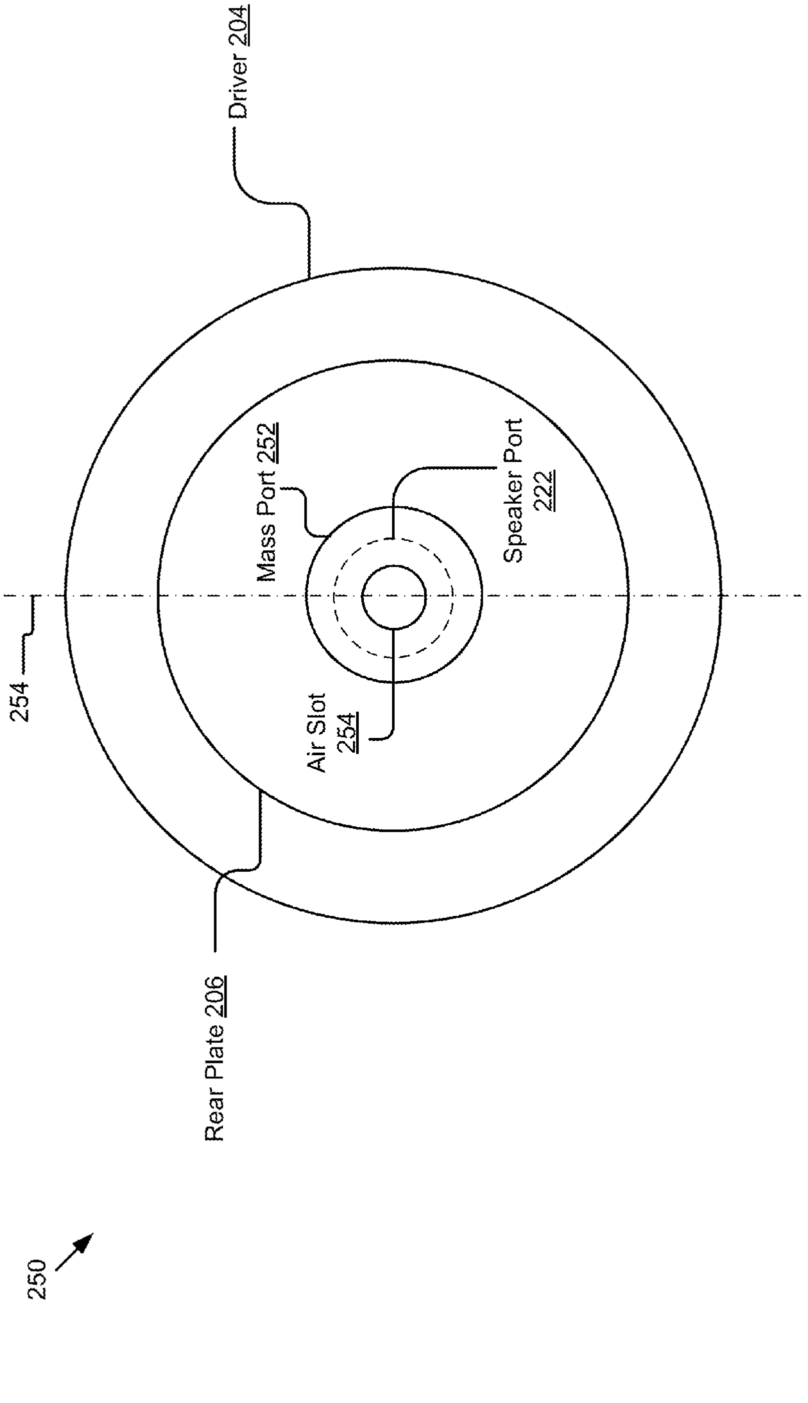
FIG. 2B illustrates an example mass port coupled to the speaker port in the rear plate of the driver of FIG. 2A according to some implementations.
Figure 2C:
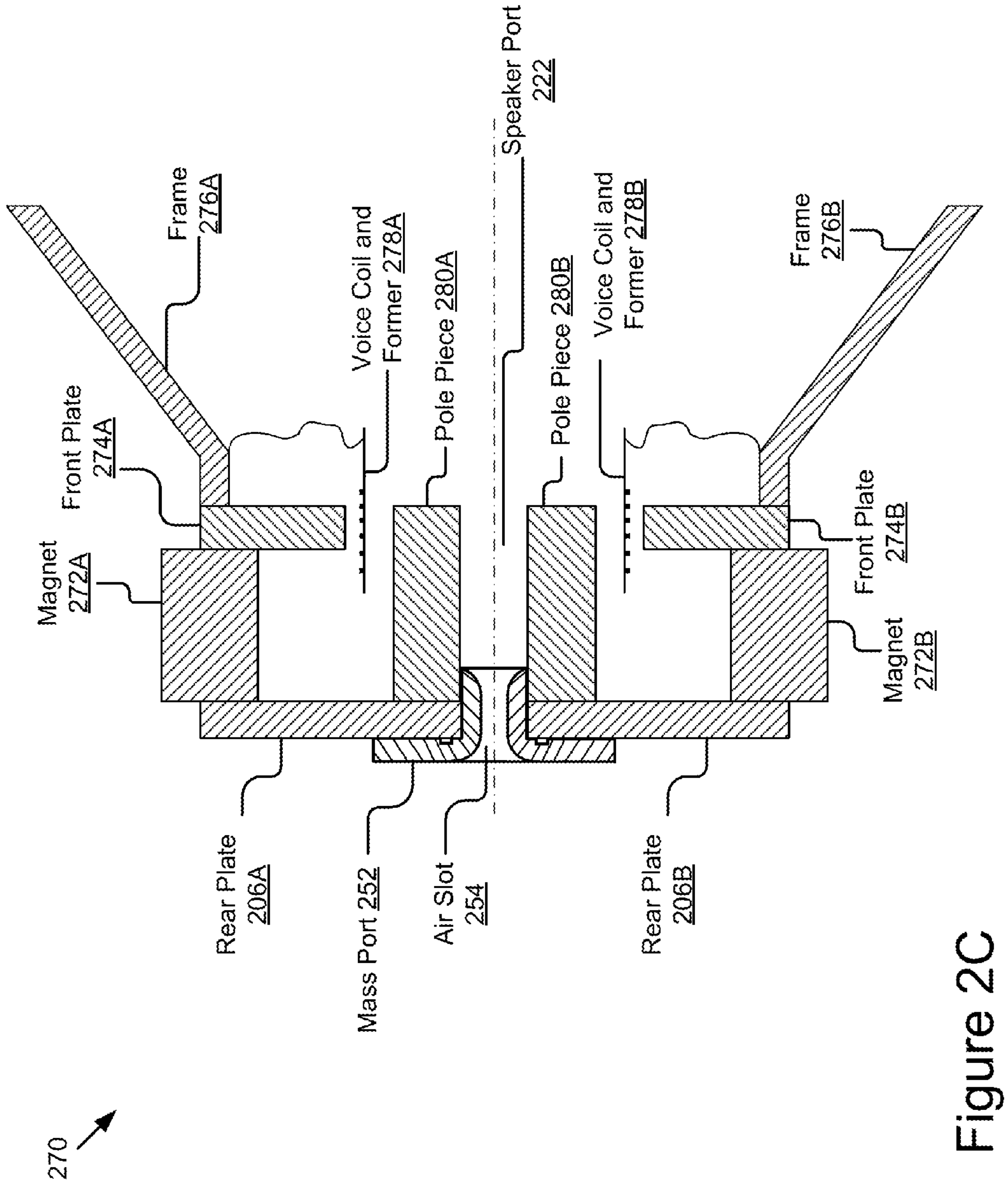
FIG. 2C illustrates a cross-sectional view of the driver and the example mass port coupled to the speaker port in the rear plate of the driver of FIG. 2B according to some implementations.

FIG. 2A illustrates a view 200 of an example speaker port 222 in a rear plate 206 of a driver 204 according to some implementations. The speaker port 222 may be a funnel that facilitates air flow between the driver 204 and a surrounding environment. The speaker port 222 may penetrate the rear plate 206.

FIG. 2B illustrates an example mass port 252 coupled to the speaker port 222 in the rear plate 206 of the driver 204 of FIG. 2A according to some implementations. The insertion portion of the mass port 252 is inserted into the speaker port 222. A cross-sectional view 270 at Section 254 is illustrated in FIG. 2C.

Turning to FIG. 2C, a cross-sectional view of the driver 204 is illustrated. The driver 204 includes the rear plate 206 (illustrated as 206A and 206B), a magnet 272 (illustrated as 272A and 272B), a pole piece 280 (illustrated as 280A and 280B), a front plate 274 (illustrated as 274A and 274B), a frame 276 (illustrated as 276A and 276B), a voice coil and former 278 (illustrated as 278A and 278B), and other suitable elements not shown in FIG. 2C. The mass port 252 of FIG. 2B may be mounted on the rear plate 206 by: (1) placing the insertion portion 104 into the speaker port 222 that penetrates the rear plate 206; and (2) gluing the rear side of the head portion 102 to the rear plate 206 using glue at the sealing structure 152. Alternatively, the mass port 252 may be attached to the rear plate 206 by pressing the insertion portion 104 into the speaker port 222 using friction, and the head portion 102 may or may not glue to the rear plate 206.

Figure 3:
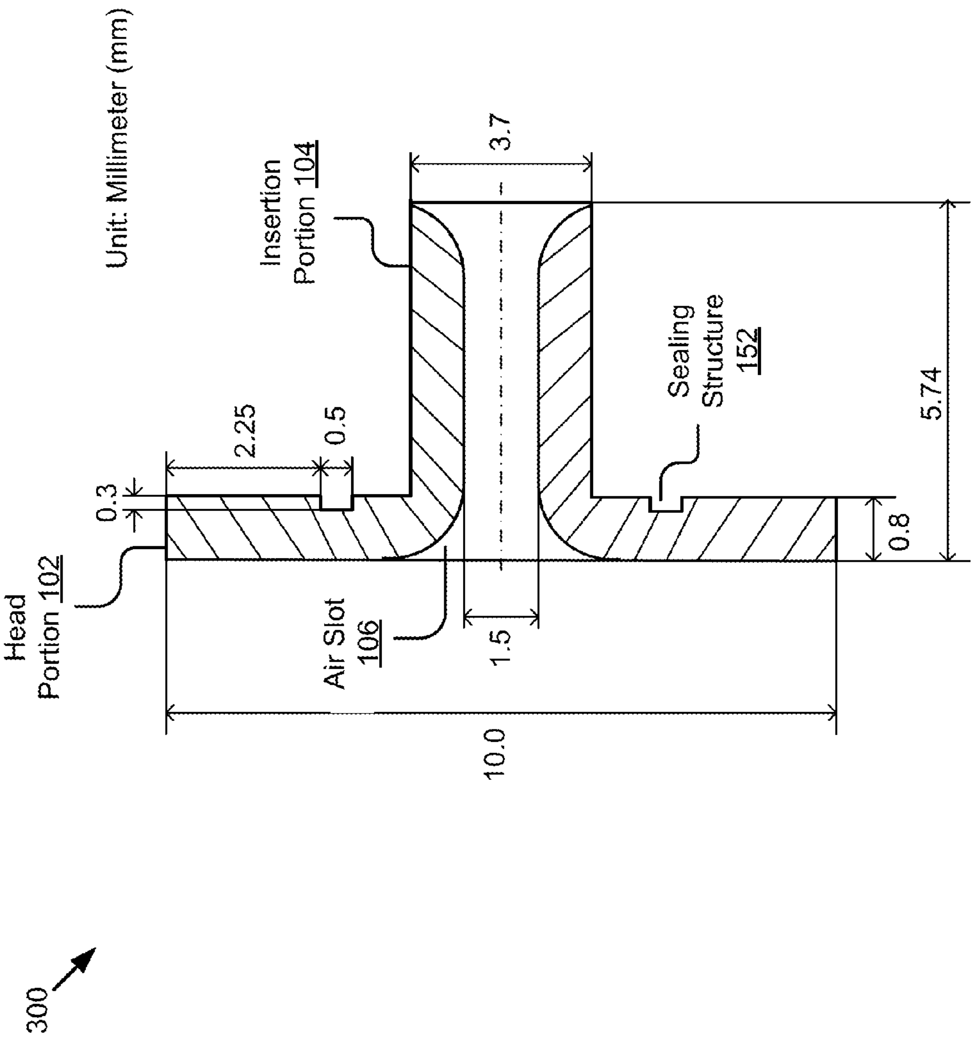
FIG. 3 illustrates a cross-sectional view of a mass port according to some implementations.

FIG. 3 illustrates a cross-sectional view 300 of a mass port according to some implementations. The head portion 102 of the mass port may have a diameter of about 10 millimeters. In some implementations, the head portion 102 may have a diameter in a range between 5 millimeters and 15 millimeters. The head portion 102 may have a thickness of about 0.8 millimeters. In some implementations, the thickness of the head portion 102 may be greater than or less than 0.8 millimeters. Other dimensions for the head portion 102 are possible.

The sealing structure 152 of the head portion 102 may have a width of about 0.5 millimeters and a depth of about 0.3 millimeters. In some implementations, the sealing structure 152 may have a width greater than or less than 0.5 millimeters and a depth greater than or less than 0.3 millimeters. A distance between the sealing structure 152 and an outer edge of the head portion 102 may be about 2.25 millimeters. In some implementations, a distance between the sealing structure 152 and the outer edge of the head portion 102 may be in a range of 1 millimeter and 3 millimeters. Other dimensions for the sealing structure 152 are possible.

The insertion portion 104 may have a diameter of about 3.7 millimeters. In some implementations, the insertion portion 104 may have a diameter in a range between 2 millimeters and 5 millimeters. A total length of the mass port may be about 5.74 millimeters, including a thickness of the head portion 102 to be about 0.8 millimeters and a length of the insertion portion 104 to be about 4.94 millimeters. In some implementations, the length of the insertion portion 104 may be a value greater than or less than 4.94 millimeters. The length of the insertion portion 104 may be a value in a range between 3 millimeters and 6 millimeters. Other dimensions for the insertion portion 104 are possible.

The air slot 106 may have a diameter of about 1.5 millimeters. The diameter of the air slot 106 may be in a range between 0.7 millimeters and 2 millimeters. The diameter of the air slot 106 may be determined based at least in part on a size of a speaker port in a rear plate of a driver. Other dimensions for the air slot 106 are possible. In some implementations, the air slot 106 may be a funnel with two conical ends.

Figure 4:
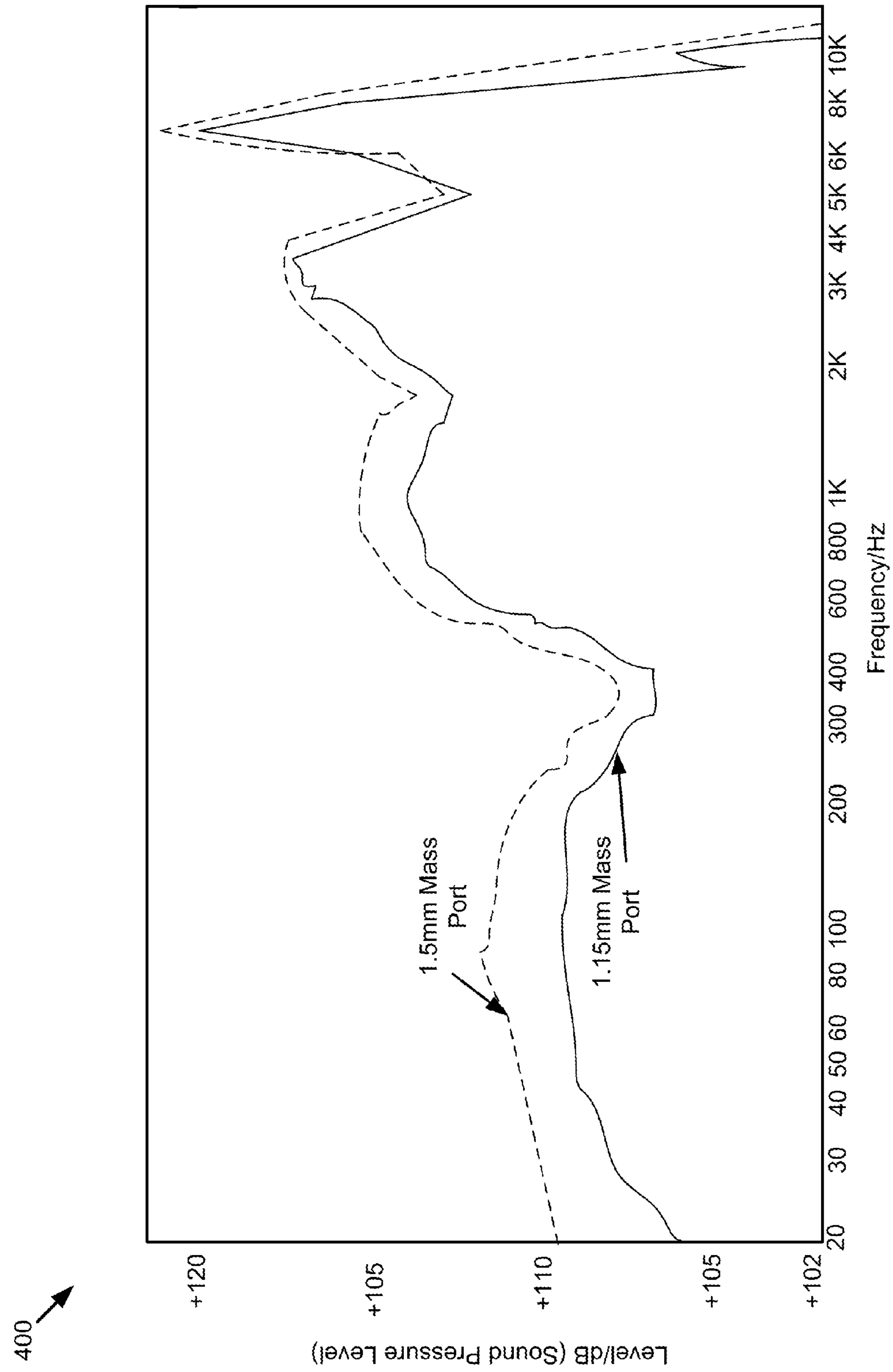
FIG. 4 is a graphic representation illustrating respective frequency responses of an audio reproduction device with mass ports that have different air slot diameters according to some implementations.

FIG. 4 is a graphic representation 400 illustrating respective frequency responses of an audio reproduction device with mass ports that have different air slot diameters according to some implementations. In some implementations, a first mass port with a diameter of 1.15 millimeters is inserted into a speaker port in a rear plate of a driver in the audio reproduction device, and a first frequency response of the audio reproduction device is measured as a solid line in FIG. 4. Next, a second mass port with a diameter of 1.5 millimeters is inserted into the speaker port in the rear plate of the audio reproduction device, and a second frequency response of the audio reproduction device is measured as a dashed line in FIG. 4. The second frequency response has a better bass quality than the first frequency response, which is achieved by increasing the diameter of the air slot from 1.15 millimeters to 1.5 millimeters. FIG. 4 illustrates that the frequency response of the audio reproduction device may be tuned by modifying the diameter of the air slot in the mass port.

Figure 5A:
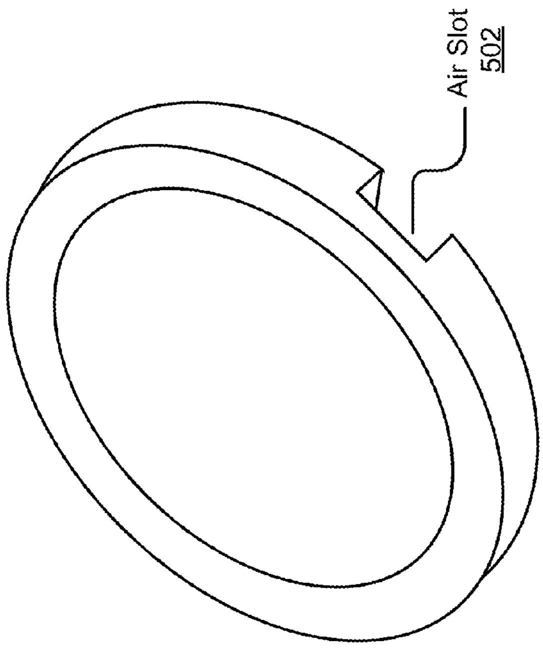
FIGS. 5A and 5B illustrate different views of another example mass port according to some implementations.
Figure 5B:
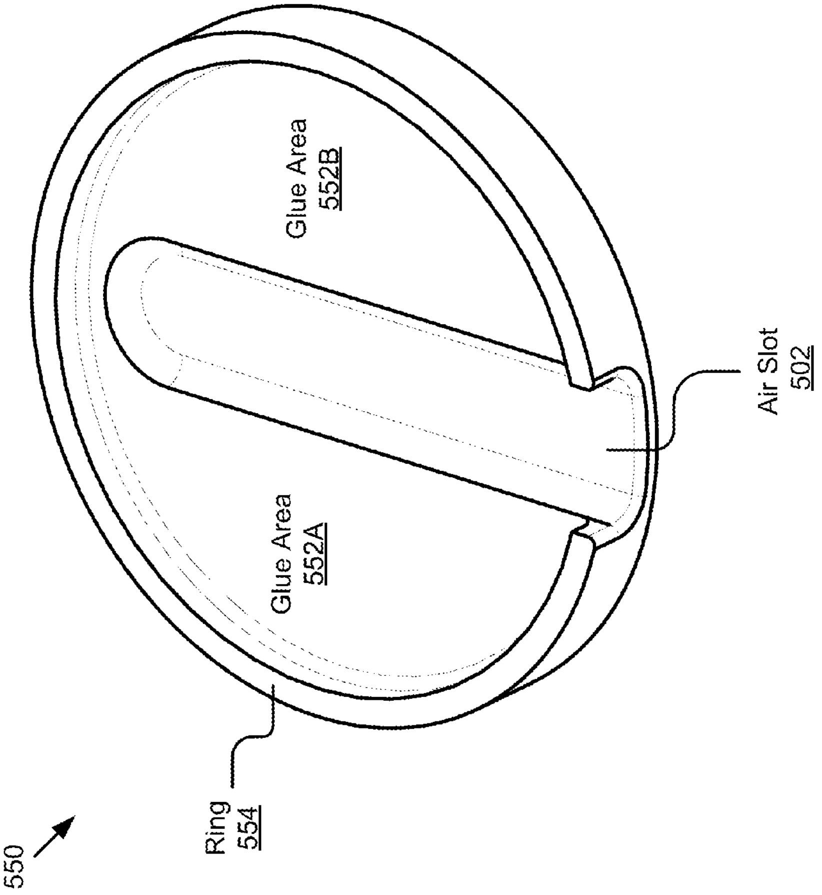

FIGS. 5A and 5B illustrate different views 500 and 550 of another example mass port according to some implementations. Referring to FIG. 5A, a front view of the mass port is illustrated. The mass port may include an air slot 502. The mass port may have a shape similar to a disc and may be referred to as a slotted disc. Additional views and dimensions of the mass port are illustrated with reference to FIGS. 7A-7C.

Referring to FIG. 5B, a rear view of the mass port of FIG. 5A is illustrated. The rear view of the mass port illustrates the air slot 502 that includes a closed end and an open end, a ring 554, and glue areas 552A and 552B. The closed end of the air slot 502 may be configured to block air flow between the air slot 502 and a surrounding environment, while the open end of the air slot 502 may be configured to allow or facilitate air flow between the air slot 502 and the surrounding environment. In the rear view of the mass port, the ring 554 surrounds the glue areas 552A and 552B, and the glue areas 552A and 552B surrounds the air slot 502. The glue areas 552A and 552B may be filled with glue to attach the mass port to the rear plate of the driver as illustrated in FIG. 6B.

Figure 6A:
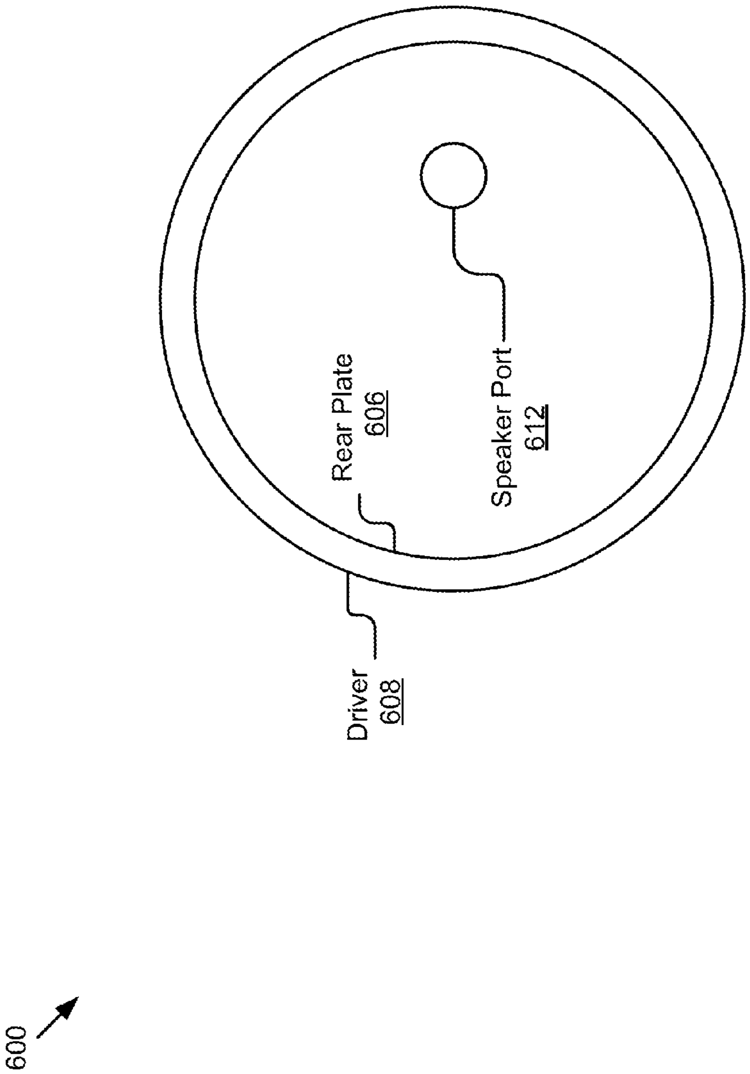
FIG. 6A illustrates an example rear plate of a driver that includes a speaker port according to some implementations.

FIG. 6A illustrates a view 600 of an example rear plate 606 of a driver 608 that includes a speaker port 612 according to some implementations. The speaker port 612 may include a funnel that penetrates the rear plate 606. A location of the speaker port 612 may not be in the center of the rear plate 606. Alternatively, the location of the speaker port 612 may be in the center of the rear plate 606.

Figure 6B:
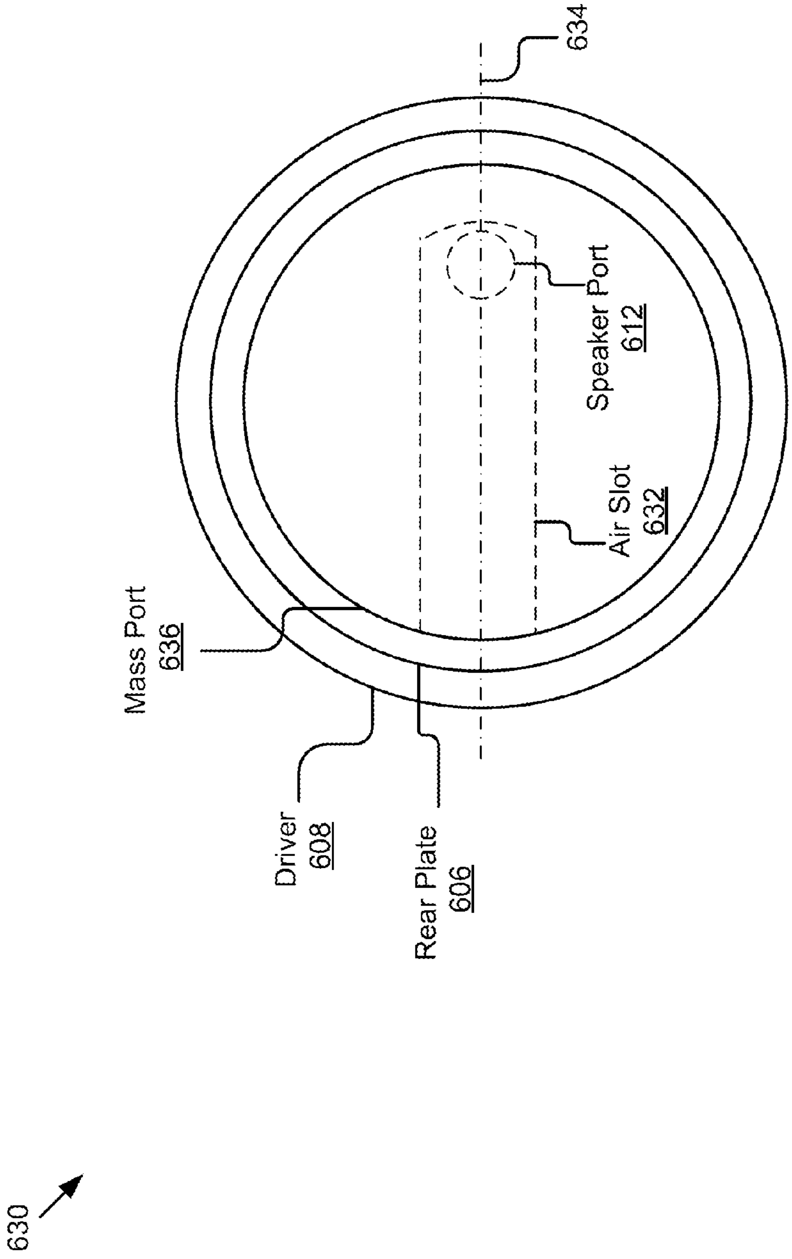
FIG. 6B illustrates an example mass port coupled to the rear plate of the driver of FIG. 6A according to some implementations.

FIG. 6B illustrates a view 630 of an example mass port 636 coupled to the rear plate 606 of FIG. 6A according to some implementations. The mass port 636 may be mounted on the rear plate 606 by gluing the rear side of the mass port 636 to the rear plate 606. Alternatively, the mass port 636 may be attached to the rear plate 606 using other mechanisms such as mechanical coupling approaches. In some implementations, a center of the mass port 636 may be configured to align with a center of the rear plate 606 so that the mass port 636 may be mounted on the rear plate 606 in balance. An air slot 632 of the mass port 636 may align with the speaker port 612 to form an air flow path. For example, a closed end of the air slot 632 may align with the speaker port 612 so that air may flow from the speaker port 612 toward the closed end of the air slot 632 and then toward an open end of the air slot 632 and vice versa. A sectional view 660 at Section 634 is illustrated in FIG. 6C.

Figure 6C:
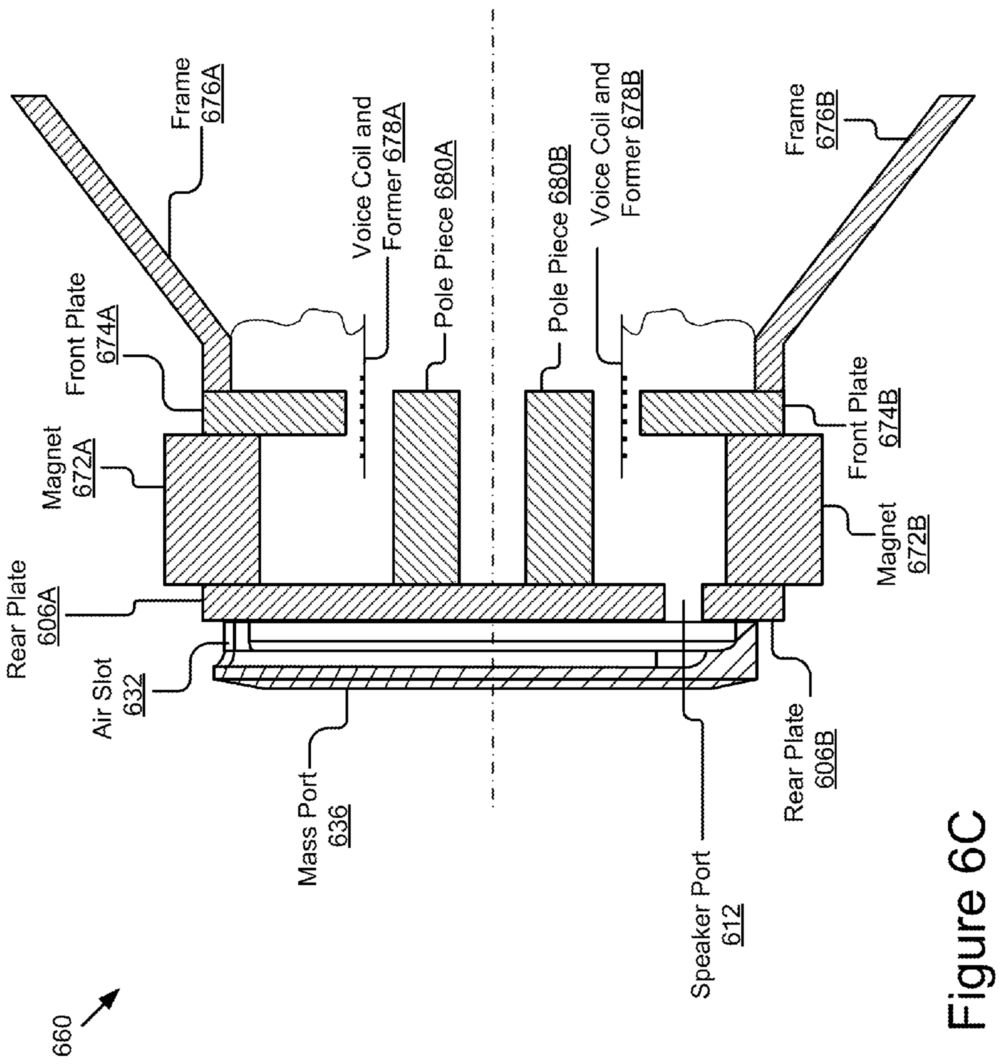
FIG. 6C illustrates a cross-sectional view of the mass port coupled to the rear plate of the driver of FIG. 6B according to some implementations.

In FIG. 6C, the mass port 636 is mounted on the rear plate 606 of the driver 608, with the closed end of the air slot 632 being aligned with the speaker port 612. The driver 608 may include the rear plate 606 (illustrated as 606A and 606B), a magnet 672 (illustrated as 672A and 672B), a pole piece 680 (illustrated as 680A and 680B), a front plate 674 (illustrated as 674A and 674B), a frame 676 (illustrated as 676A and 676B), a voice coil and former 678 (illustrated as 678A and 678B), and other suitable elements not shown in FIG. 6C.

Figure 7A:
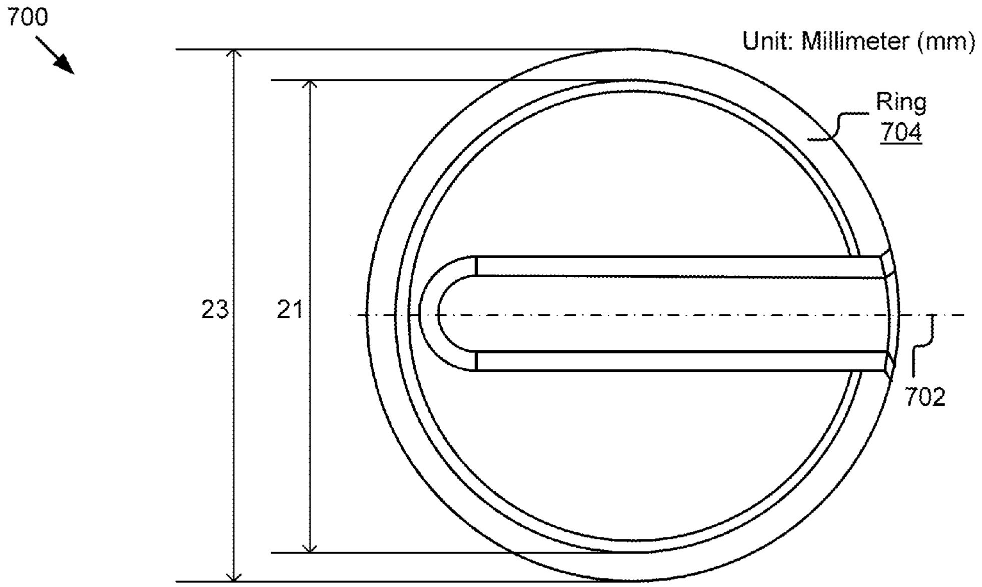
FIG. 7A illustrates a rear view of a mass port according to some implementations.

FIG. 7A illustrates a rear view 700 of a mass port according to some implementations. A ring 704 of the mass port may have an outer diameter of about 23 millimeters and an inner diameter of about 21 millimeters. In some implementations, the outer diameter of the ring 704 may have a value in a range between 10 millimeters and 30 millimeters. The inner diameter of the ring 704 may have a value in a range between 8 millimeters and 28 millimeters. Other dimensions for the outer diameter and inner diameter of the ring 704 are possible. A sectional view of the mass port at Section 702 is illustrated with reference to FIG. 7C.

Figure 7B:
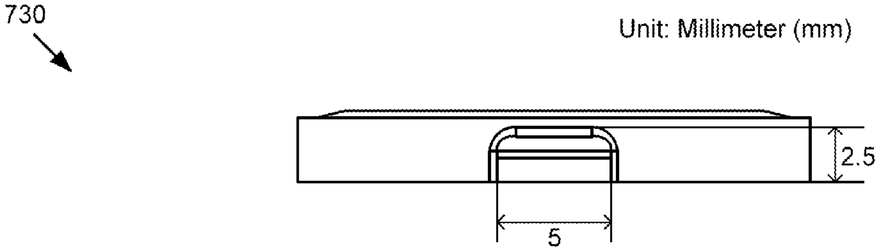
FIG. 7B illustrates a side view of the mass port of FIG. 7A according to some implementations.

FIG. 7B illustrates a side view 730 of the mass port of FIG. 7A according to some implementations. The side view 730 illustrates an air slot of the mass port with a width of about 5 millimeters and a height of about 2.5 millimeters. The width of the air slot may have a value in a range between 2 millimeters and 10 millimeters. The height of the air slot may have a value in a range between 1.5 millimeters and 3 millimeters. Other dimensions for the width and height of the air slot are possible. In some implementations, the height of the air slot in the mass port may be modified to tune a frequency response of an audio reproduction device that the mass port is mounted on.

Figure 7C:
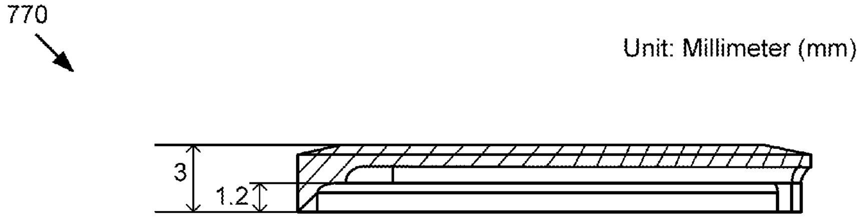
FIG. 7C illustrates a cross-sectional view of the mass port of FIG. 7A according to some implementations.

FIG. 7C illustrates a cross-sectional view 770 of the mass port of FIG. 7A according to some implementations. The mass port may have a height or a thickness of about 3 millimeters. In some implementations, the mass port may have a height value in a range between 2 millimeters and 5 millimeters. Other dimensions for the height of the mass port are possible. The cross-sectional view 770 also illustrates a depth for the glue areas in the mass port to be about 1.2 millimeters. In some implementations, the depth for the glue areas may have a value in a range between 1 millimeter and 2 millimeters. Other dimensions for the depth of the glue areas are possible.

Examples of mass ports for tuning frequency responses of audio reproduction devices are described above. In the foregoing description, for purposes of explanation, numerous specific details are set forth in order to provide a thorough understanding of the specification. It will be apparent, however, to one skilled in the art that the implementations can be practiced without these specific details. In other instances, structures and devices are shown in block diagram form in order to avoid obscuring the specification. For example, the specification is described in one implementation below with reference to particular hardware. However, the description applies to any type of speaker drivers.

Reference in the specification to "one implementation" or "an implementation" means that a particular feature, structure, or characteristic described in connection with the implementation is included in at least one implementation. The appearances of the phrase "in one implementation" in various places in the specification are not necessarily all referring to the same implementation.

It should be borne in mind, however, that all of these and similar terms are to be associated with the appropriate physical quantities and are merely convenient labels applied to these quantities. The specification also relates to an apparatus for implementing the disclosure described herein. For example, this apparatus may be specially constructed for the required purposes.

The present disclosure can be applied to all sizes and types of linear magnetic actuators, both audio and non-audio. This includes the full range of audio transduction devices: tweeter; midrange; woofer; headphone; earbuds; and microphone, etc. The present disclosure is also applicable to non-standard audio transducers that utilize current-carrying wires disposed in magnetic gaps. The present disclosure may also be applied in any other magnetic circuit design. An example of a non-audio linear actuator includes a permanent-magnet synchronous motor. A person having ordinary skill in the art will appreciate that there are other non-audio linear actuators.

The foregoing description of the implementations has been presented for the purposes of illustration and description. It is not intended to be exhaustive or to limit the specification to the precise form disclosed. Many modifications and variations are possible in light of the above teaching. It is intended that the scope of the implementations be limited not by this detailed description, but rather by the claims of this application. As will be understood by those familiar with the art, the examples may be embodied in other specific forms without departing from the spirit or essential characteristics thereof. Likewise, the particular naming and division of the modules, routines, features, attributes, methodologies and other aspects are not mandatory or significant, and the mechanisms that implement the description or its features may have different names, divisions and/or formats. Furthermore, as will be apparent to one of ordinary skill in the relevant art, the modules, routines, features, attributes, methodologies and other aspects of the specification can be implemented as software, hardware, firmware or any combination of the three. Accordingly, the disclosure is intended to be illustrative, but not limiting, of the scope of the specification, which is set forth in the following claims.

What is claimed is:

1. A mass port comprising:

an insertion portion having an elongated cylindrical shape having a longitudinal axis and configured to be inserted into a speaker port on a rear plate of a driver, the insertion portion including a diameter between 2 millimeters and 5 millimeters and a length between 3 millimeters and 6 millimeters;

a head portion having a disc shape with a front side and a rear side, the head portion integrally coupled with the insertion portion such that the insertion portion extends from the rear side of the head portion, the head portion including a diameter between 5 millimeters and 10 millimeters, the head portion further comprising:

a sealing structure formed within the rear side of the head portion, and configured to attach the mass port to the rear plate of the driver; and an air slot that runs through a center of the head portion and a center of the insertion portion along the longitudinal axis of the insertion portion, the air slot including a diameter between 0.75 millimeters and 2 millimeters.

2. A mass port comprising:

a head portion including a sealing structure formed into a rear side of the head portion, the head portion configured to attach to a rear plate of a driver at the sealing structure; and an insertion portion integrally coupled with the rear side of the head portion, the insertion portion configured to be inserted into a speaker port on the rear plate of the driver, the head portion and the insertion portion including an air slot that runs through the head portion and the insertion portion.

3. The mass port of claim 2, wherein the head portion includes a disc and the air slot penetrates a center of the disc.

4. The mass port of claim 3, wherein the disc includes a diameter of 10 millimeters and a thickness of 0.8 millimeters.

5. The mass port of claim 2, wherein the insertion portion includes a cylinder and the air slot penetrates a center of the cylinder along a longitudinal axis of the cylinder.

6. The mass port of claim 5, wherein the cylinder includes a diameter of 3.7 millimeters and a length of 4.94 millimeters.

7. The mass port of claim 2, wherein the head portion and the insertion portion are formed by a single piece of material.

8. The mass port of claim 7, wherein the single piece of material includes a piece of plastic.

9. The mass port of claim 2, wherein the air slot includes a diameter of 1.5 millimeters.

10. The mass port of claim 2, wherein the air slot includes a diameter in a range between 0.75 millimeters and 2 millimeters.

11. The mass port of claim 2, wherein the sealing structure includes a glue moat.

12. The mass port of claim 11, wherein the glue moat is filled with glue, and includes a width of 0.5 millimeters and a depth of 0.3 millimeters.

13. The mass port of claim 11, wherein a distance between an outer edge of the head portion and the glue moat includes 2.25 millimeters.

14. The mass port of claim 2, wherein a size of the air slot is configured to be modifiable to tune a frequency response of the driver.

15. The mass port of claim 2, wherein the air slot includes a funnel with two conical ends.

16. The mass port of claim 2, wherein the size of the air slot is configured to increase the bass present in a frequency response of the driver.

17. A mass port comprising:

a head portion having a disc shape with a front side and a rear side, the rear side comprising:

a ring structure integrally formed with the head portion, circumscribing the circumference of the head portion, and extending perpendicularly from the rear side of the head portion;

an air slot formed within the rear side of the head portion, the air slot including a closed end and an open end, the open end formed within a portion of the ring structure and the closed end disposed within an area of the rear side of the head portion circumscribed by the ring portion;

a first glue area on the rear side of the head portion disposed within an area of the rear side of the head portion circumscribed by the ring structure, the first glue area comprising a flat surface; and a second glue on the rear side of the head portion disposed within an area of the rear side of the head portion circumscribed by the ring structure, the second glue area comprising a flat surface.

18. The mass port of claim 17, wherein the closed end of the air slot is configured to block air flow between the air slot and a surrounding environment, and the open end of the air slot is configured to allow air flow between the air slot and the surrounding environment.

19. The mass port of claim 17, wherein the air slot has a width between 2 millimeters and 10 millimeters, and a height between 1.5 millimeters and 3 millimeters.

20. The mass port of claim 17, wherein the mass port is configured to be mounted on a rear plate of a driver by gluing the rear side of the mass port to the rear plate.

* * * * *